(12) United States Patent
Demsia

(10) Patent No.: US 12,187,994 B2
(45) Date of Patent: Jan. 7, 2025

(54) TWO POSITION SCREW CAP CULTURE TUBE

(71) Applicant: Walter Demsia, Sayreville, NJ (US)

(72) Inventor: Walter Demsia, Sayreville, NJ (US)

( * ) Notice: Subject to any disclaimer, the term of this patent is extended or adjusted under 35 U.S.C. 154(b) by 836 days.

(21) Appl. No.: 16/843,806

(22) Filed: Apr. 8, 2020

(65) Prior Publication Data

US 2020/0318046 A1    Oct. 8, 2020

Related U.S. Application Data

(60) Provisional application No. 62/831,162, filed on Apr. 8, 2019.

(51) Int. Cl.
| | | |
|---|---|---|
| *C12M 1/24* | (2006.01) | |
| *C12M 1/00* | (2006.01) | |
| *C12M 1/12* | (2006.01) | |

(52) U.S. Cl.
CPC ............ *C12M 23/08* (2013.01); *C12M 23/38* (2013.01); *C12M 37/04* (2013.01)

(58) Field of Classification Search
None
See application file for complete search history.

(56) References Cited

U.S. PATENT DOCUMENTS

| | | | | |
|---|---|---|---|---|
| 4,289,248 | A  * | 9/1981 | Lynn ................. | B65D 41/0471 215/331 |
| 5,192,511 | A  * | 3/1993 | Roach ................. | B01L 3/0279 73/864.11 |
| 6,085,922 | A  * | 7/2000 | Esser ................ | B65D 51/1688 215/354 |
| 2010/0196871 | A1 * | 8/2010 | Dodgson ............... | C12M 21/08 435/284.1 |

OTHER PUBLICATIONS

English Abstract of RU 173302 provided by USPTO, original document published 2017 (Year: 2017).*
"Tube ." Merriam-Webster's Collegiate(R) Dictionary, 11th ed., Merriam-Webster, 2012. Credo Reference https://search.credoreference.com/articles/Qm9va0FydGljbGU6MjUxMjg1?aid=279753 (Year: 2012).*

* cited by examiner

*Primary Examiner* — Holly Kipouros
(74) *Attorney, Agent, or Firm* — FisherBroyles, LLP; Susan M. Oiler

(57) ABSTRACT

A two-position screw cap culture tube includes a snapping ring on the tube, with a pair of recesses in the snapping ring that provide an aerobic clearance, and a snap groove on the cap. The snap groove engages with the snapping ring when the cap is screwed into a first position that provides a second aerobic clearance between the top of the tube and the cap, to provide an air path and an aerobic culturing system. The snap groove disengages with the snapping ring and the tube is pressed against the underside of the cap to block the air path and provide an anaerobic culturing system.

11 Claims, 5 Drawing Sheets

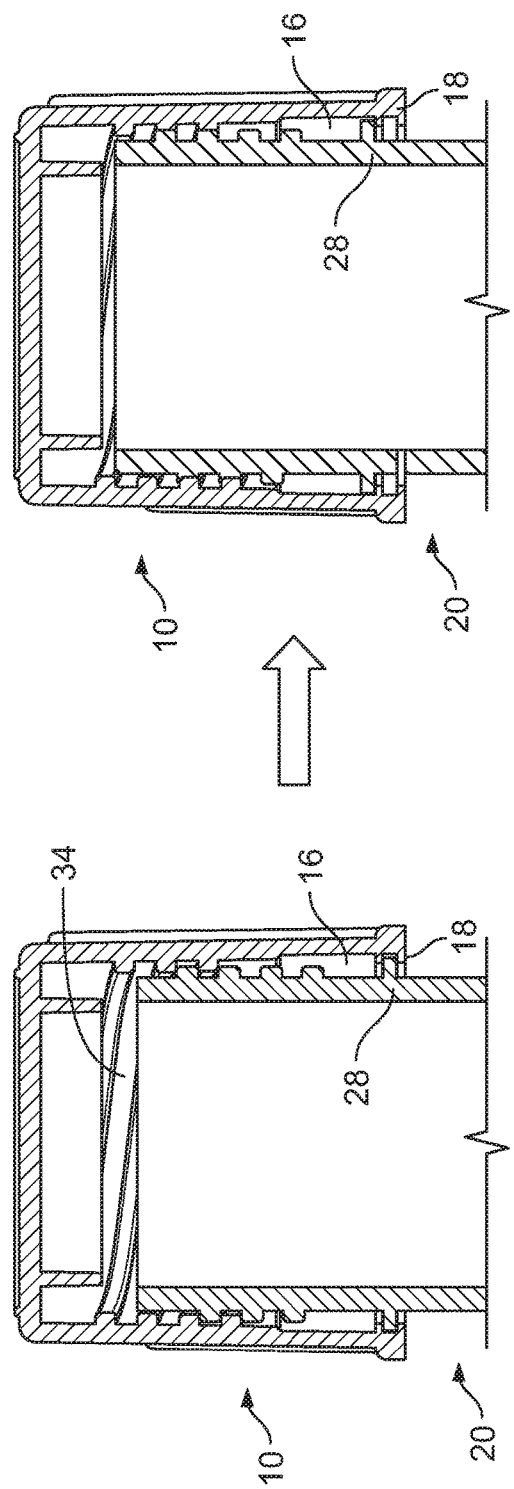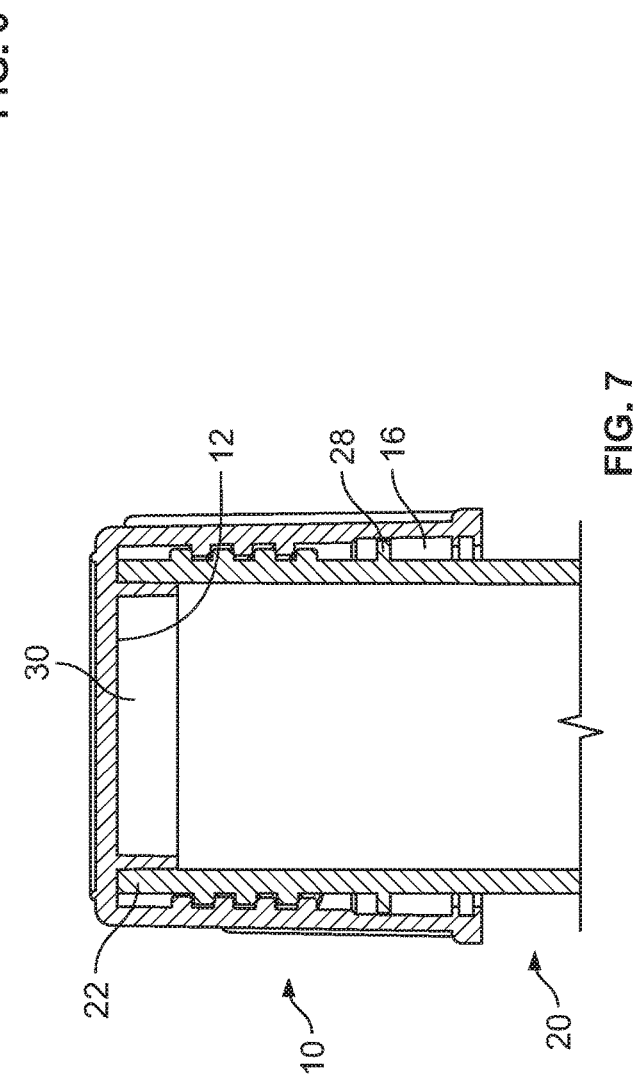

TWO POSITION SCREW CAP CULTURE TUBE

RELATED APPLICATIONS

This application claims the benefit of the filing date of U.S. Patent Application No. 62/831,163, filed Apr. 8, 2019, which is incorporated herein by reference in its entirety.

BACKGROUND OF THE INVENTION

The present invention generally relates to test tubes and more specifically to a two-position screw-cap culture tube.

Existing culture tubes and caps for aerobic and/or anaerobic culturing may require cap that fits onto the tube in an airtight fashion or in a fashion that allows air to enter and exit (exchange) through areas between the vertical ribs of the cap. These are commonly known as dual position or two position caps, friction-fit caps, or snap-caps. These caps can be moved up or down vertically in either of two positions.

It would be desirable to have a culture tube that provides both an aerobic and an anaerobic culture system, without requiring a friction-fit snap-cap that only moves up or down vertically.

SUMMARY OF THE INVENTION

In one aspect of the present invention, a culturing system comprises a tube with tube walls, a tube rim, and tube threads on the walls; a cap that fits over the tube rim, having a cap underside and cap threads that engage with the tube threads so as to screw the cap down onto the tube; a snapping ring on the tube, with at least one recession in the snapping ring that provides a first aerobic clearance between the walls of the tube and the cap; a snap groove on the cap that engages with the snapping ring when the cap is screwed into a first position that provides a second aerobic clearance between the tube rim and the cap underside, cooperating with the first aerobic clearance to provide an air path and an aerobic culturing system; and wherein the snap groove disengages with the snapping ring when the cap is screwed into a second position, so that the tube rim is pressed against the cap underside to seal the first aerobic clearance, thereby blocking the air path to provide an anaerobic culturing system.

In another aspect of the present invention, a method of closing a cap to a tube comprises placing a threaded cap on to a threaded end of a tube; turning the cap; identifying a first area of friction, thereby achieving an aerobic position where the tube is attached to the cap but unsealed; further turning the cap; and identifying a second area of friction, thereby achieving an anaerobic position where the tube is fully sealed.

BRIEF DESCRIPTION OF THE DRAWINGS

FIG. 6 depicts a side view of the embodiment of FIG. 1 transitioning from an aerobic position into an anaerobic position.

FIG. 7 depicts a side view of the embodiment of FIG. 1 in a fully anaerobic position.

DETAILED DESCRIPTION

Figure 1:
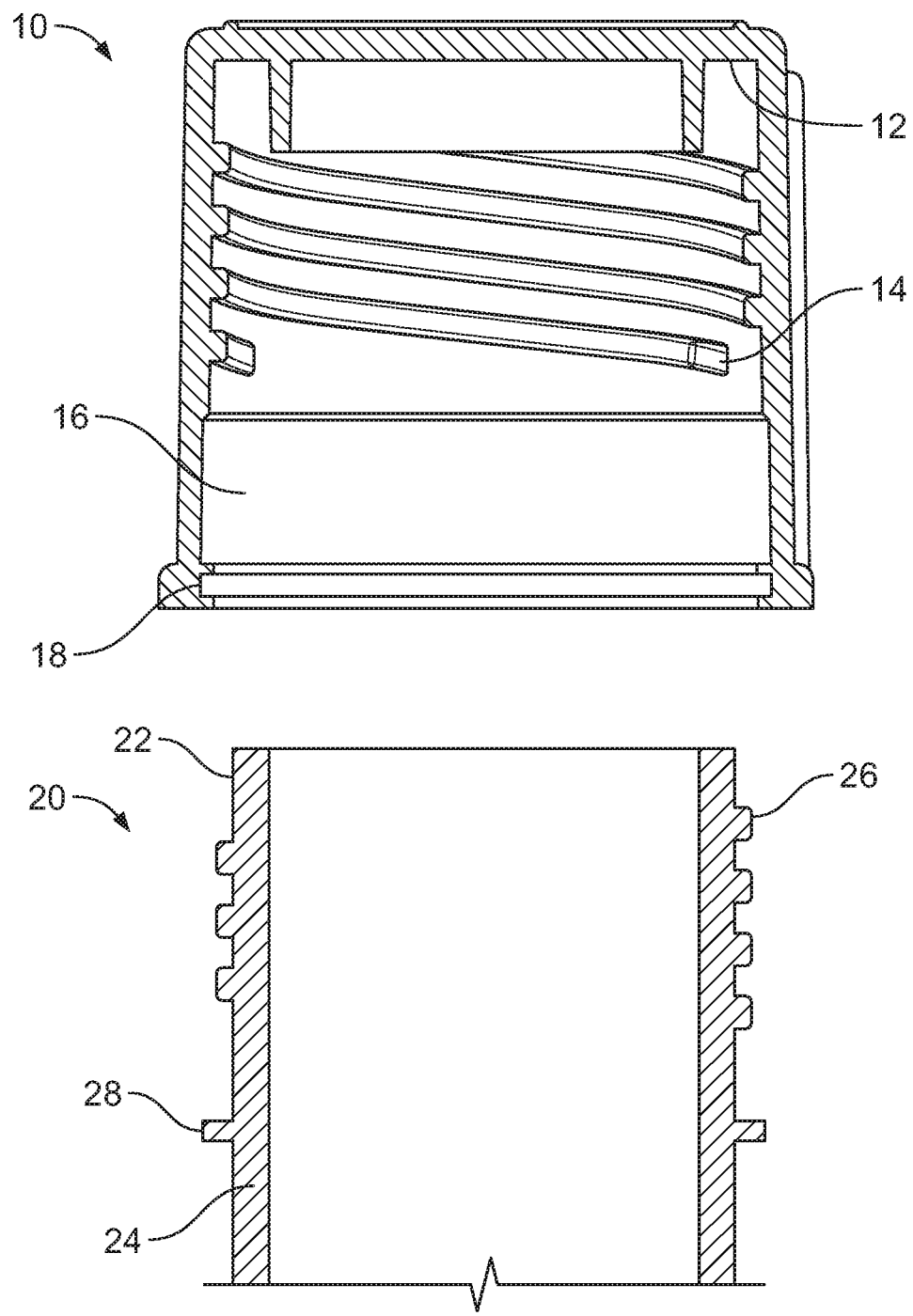
FIG. 1 depicts a side view of an embodiment of a cap and tube according to the present invention.

The preferred embodiment and other embodiments, which can be used in industry and include the best mode now known of carrying out the invention, are hereby described in detail with reference to the drawings. Further embodiments, features and advantages will become apparent from the ensuing description, or may be learned without undue experimentation. The figures are not necessarily drawn to scale, except where otherwise indicated. The following description of embodiments, even if phrased in terms of "the invention" or what the embodiment "is," is not to be taken in a limiting sense, but describes the manner and process of making and using the invention. The coverage of this patent will be described in the claims. The order in which steps are listed in the claims does not necessarily indicate that the steps must be performed in that order.

An embodiment of the present invention generally provides a plastic culture tube with screw cap, where there may be two positions for the cap on the tube that relate to air-flow. The first position snaps the cap onto the tube, but still allows air-flow into the culture tube. When the cap is further twisted, the tube fully closes into an air-tight seal. Embodiments of the present invention may set up an aerobic/anaerobic culture environment using a multiple position screw thread, without requiring an up-and-down snap cap. Embodiments may have various plastic materials in at least two sizes, including 12×75 mm or 17×100 mm tubes with appropriately-sized caps.

In an embodiment, the user may place a cap on to the threaded end of a culture tube and begin to turn the cap clockwise. An area of friction (a first "bump") may be felt very soon into the first turn. Once that area of friction is past, the cap may now be firmly attached in an aerobic position to allow breathing of the tube's contents. The cap will tend not to fall off, be shaken off, or become otherwise detached. Embodiments may allow air to flow in and out of the tube, and if turned upside down, the liquid may slowly spill out. If one continues turning the cap an additional few degrees, a second area of friction may be felt. Turning past that second bump may allow the user to continue turning another half turn, at which point the cap may form an airtight and liquid-tight seal like any ordinary screw cap.

In an embodiment, before a cap-and-tube system is in the first position, a user may put the cap on the tube and then turn the screw cap down onto the tube until the user feels the first area of friction (resistance to turning the cap). When the user turns the cap further, the snapping ring is forced into the ring grove, causing a clicking noise and a sudden release of resistance. The user can easily tell when the cap is snapped into the first position. The cap (in the first position) is attached to the tube, but there is still an airway to the contents of the test tube. If the tube were set on its side or dumped over, the contents of the tube would probably spill out.

In an embodiment, the user may initially start to screw the cap onto the tube ("zero" position). In the first position, the snapping ring holds the cap at a precise distance so that air flows from the outside into the tube (perhaps according to FDA regulations). The snapping ring on the tube will snap into the snap groove of the cap, then pop out of the groove and into the snap ring chamber, and then travel up (not necessarily to the top). The ring of the tube will stop travelling upwards in the cap chamber when the tube rim meets the cap underside, resulting in the sealed position of the culture system. In this second position, the cap may form a seal with a mating ring on the underside of the cap. The mating ring extension to the cap may provide additional surface area to enhance contact and improve the seal between the cap and tube.

In embodiments, the first frictional position is secure, but not air tight. This is because there is a clearance between the tube rim and underside of the cap. A snap groove (a radial, uniform groove on the circular inside surface of the cap) holds the cap to the snapping ring on the tube, but also provides an airway. Air can flow into the tube through the first-position cap clearance, and also through the recesses in the snapping ring. The tube contents are open to the air until the user snaps it out of the first position, further twists the cap, and seals the system in a second position. The user can tell when the cap is tight (as in a typical screw cap) from the increased resistance to tightening.

Embodiments of a plastic cap may be reinforced around the snap groove, to provide support and room for the snapping ring.

Embodiments of caps may have ridges or small flanges on the outside, to help the user twist the cap.

Embodiments of the tube rim and cap underside may be flat, and the screw threads of the tube (tube threads) may correspond to and engage with the screw threads of the cap (cap threads). This may be consistent with commercial standards for flightings and threads of existing screw-caps and culture tubes.

Embodiments may give an additional visual indication to the user as to whether the system is in an aerobic or anaerobic position.

Embodiments of a two-position system, capable of both anaerobic and aerobic uses, may comply with standards for culture tube sizes and the machines that utilize test tubes. Embodiments may include (for example) 12×75 mm or 17×100 mm tubes.

FIG. 1 depicts an embodiment of a cap 10 and a tube 20. Cap 10 may have an underside 12, interior cap threads 14 which go down part of the way down the interior side of the cap, a snap ring chamber 16, and a snap groove 18 near the bottom. Tube 20 may have tube rim 22, tube walls 24 with exterior tube threads 26, and a snapping ring 28.

Figure 2:
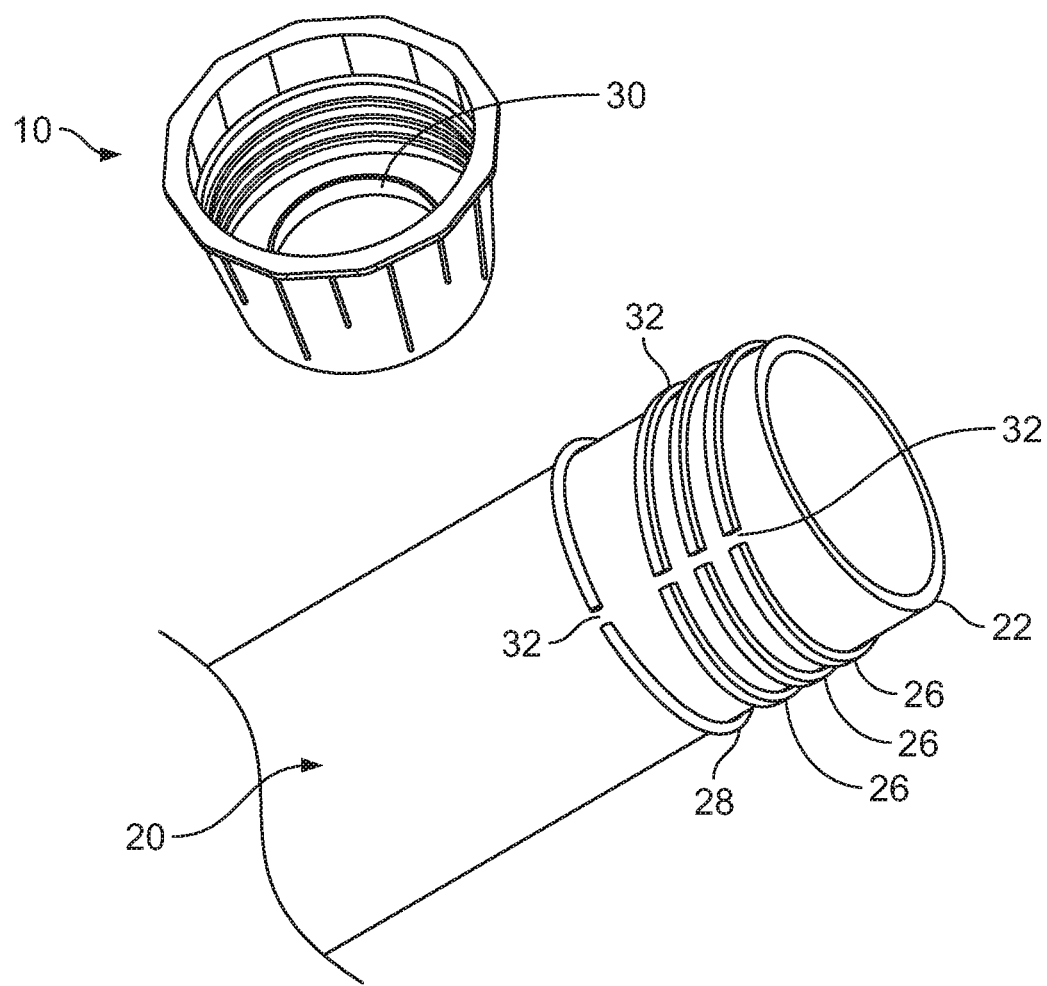
FIG. 2 depicts an oblique view of the cap and tube embodiment of FIG. 1.

FIG. 2 depicts an embodiment of a cap 10 having a mating ring 30 on the cap underside that fits inside tube 20 to form the seal with the tube rim 22. Embodiments of a tube 20 may have recesses 32 or other aerobic clearances on the snapping ring 28 and tube threads 26, to form an air-path up the side of the tube to the tube rim.

Figure 3A:
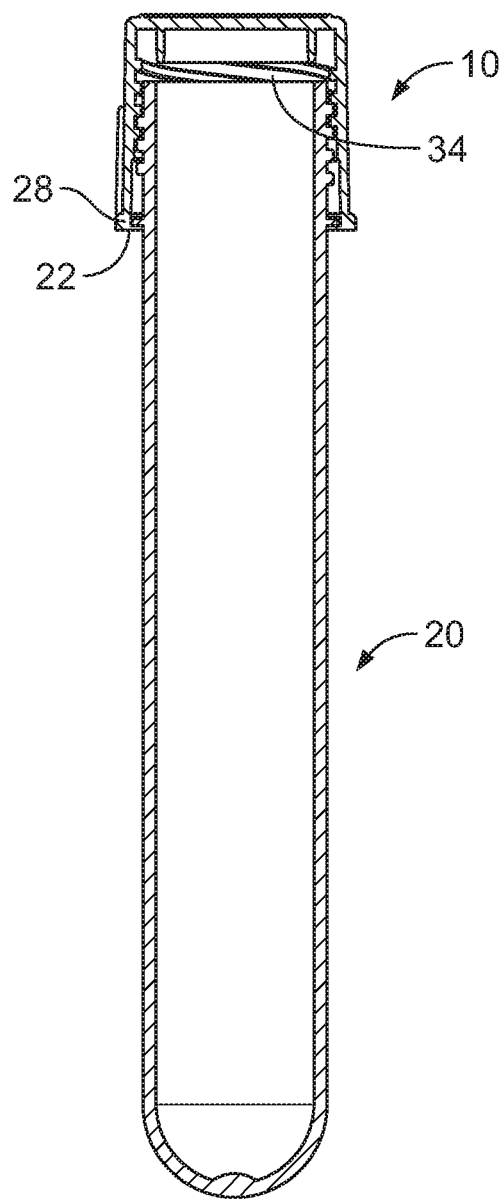
FIG. 3A depicts a side view of the embodiment of FIG. 1, with the cap and tube attached together.

FIG. 3A depicts tube 20 with a cap 10 attached in a first, aerobic position, having a clearance 34 at the top of the tube. Snapping ring 28 is engaged with tube rim 22, yet the structure keeps a clear air-path so air can still get into the test tube. The structure alongside the walls of the tube keeps an open air-path, so the system is ready for aerobic (with-air) culturing.

Figure 3B:
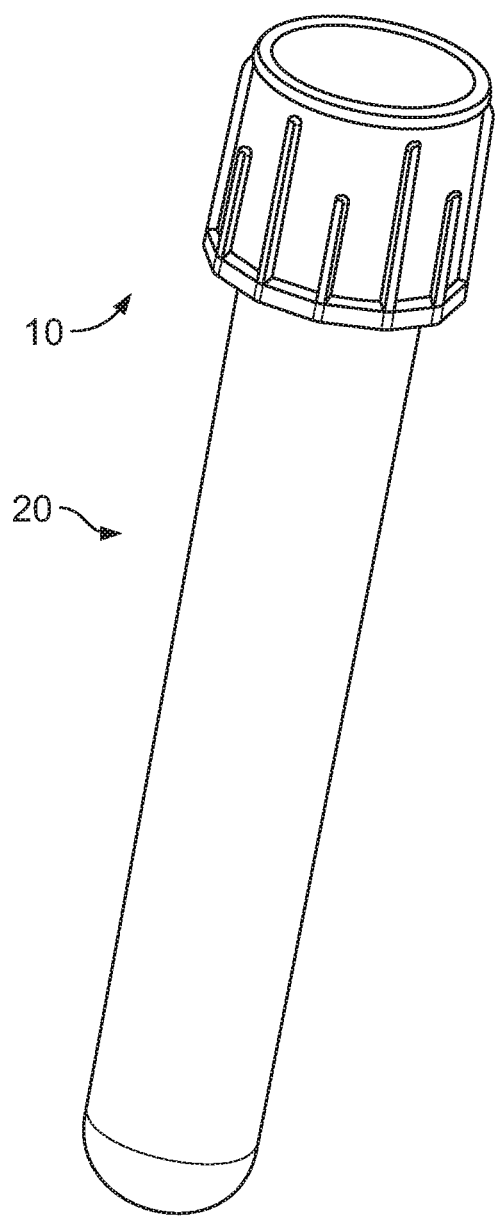
FIG. 3B depicts an oblique view of the embodiment depicted in FIG. 3A.

FIG. 3B depicts the tube and cap system, which may be twisted into either an aerobic or anaerobic position without completely opening the tube.

Figure 4:
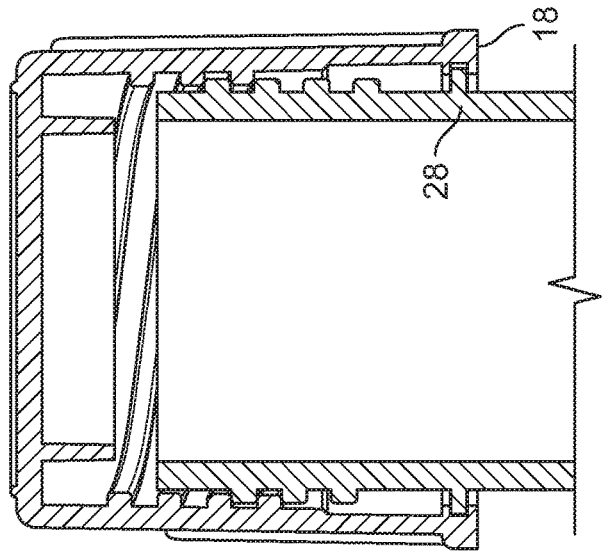
FIG. 4 depicts a side view of the embodiment of FIG. 1 transitioning into an aerobic position.
Figure 4:
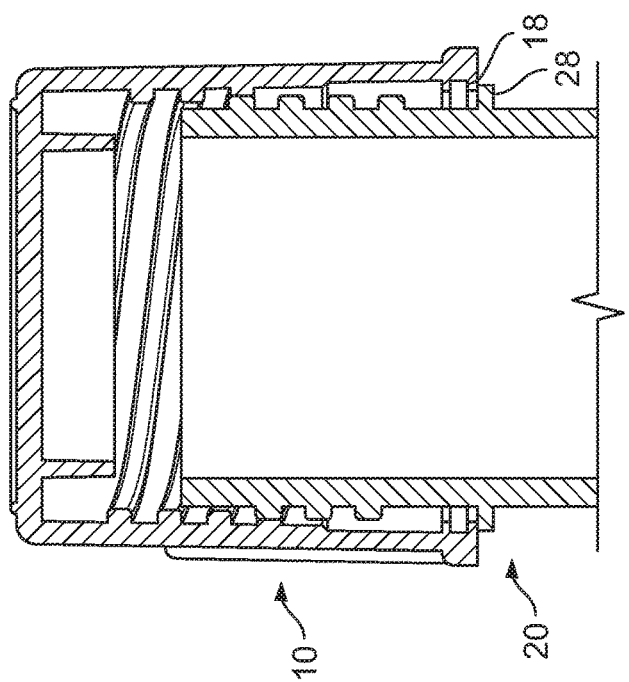

FIG. 4 depicts a tube 20 and cap 10 in an unsecured, fully-open position (depicted on the left), transitioning into a secured-but-aerobic position (right). On the left, snapping ring 28 of the tube is not yet engaged with snap groove 18 of the cap. On the right, the snapping ring 28 has been forced by the user into the first groove. The aerobic position (right) still has an aerobic clearance 34 at the top of the tube, because the snap groove 18 holds the snapping ring 28 in place, and the cap will not screw down any lower without the user feeling that the cap is going past the snap.

Figure 5:
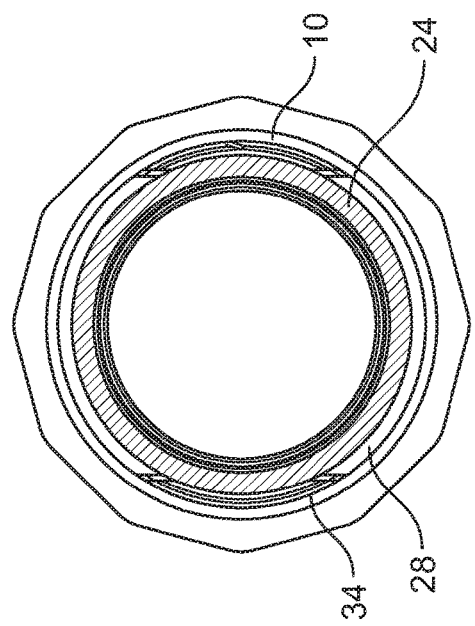
FIG. 5 depicts a top view of the embodiment of FIG. 1 with the cap and tube attached together.

FIG. 5 depicts embodiments of recesses in the snapping ring. A preferred embodiment has two recesses 34 in the threads and flightings on the sides of the snapping ring 28, which engage with the interior cap threads but keep an air pathway alongside the tube. The recesses 34 provide an aerobic air pathway alongside the walls of the tube 24 and the cap 10. The pathway may be sealed by further twisting the cap and closing the top of the tube, but if there is a clearance at the top, the air pathway to the contents of the tube remains open.

FIG. 6 depicts a tube 20 and cap 10 in a secured-but-aerobic position (left) transitioning into a fully-sealed-anaerobic (right) position. The left side of FIG. 6 is the same as the right-side of FIG. 4, where the snapping ring 28 on the tube is engaged with the snap groove 18 of the cap. There is a clearance 34 at the top of the tube. The snap ring chamber 16 is empty.

The right side of FIG. 6 shows that the cap 10 has been screwed further down onto tube 20, so that snap groove 18 and snapping ring 28 have disengaged. The snapping ring 28 is in the snap ring chamber 16 of the cap, and if the user twists the cap, the snapping ring 28 (a flange partway down the exterior of the tube) will slide up and down within the snap ring chamber 16 (an open area inside the cap between the ring groove and the cap threads). When tube 10 rises, tube rim 22 will approach cap underside 12. When the clearance 34 at the top of the tube is eliminated, the cap and tube will press flush together to create second position having an air-tight seal. The user can detect this second position from the resistance to torque which happens when any screw-cap is twisted until tight.

FIG. 7 shows a cap 10 screwed all the way into an anaerobic position. Cap underside 12 may have a plastic, flexible mating ring 30 that engages with tube 20 and forms a seal with tube rim 22. Snapping ring 28 on the tube may be retained within ring chamber 16 of the cap, preferably near or at the top of the chamber.

I claim:

1. A method of closing a cap to a tube, comprising:
   placing a threaded cap on to a threaded end of a tube;
   turning the cap;
   identifying a first area of friction which defines a first position of the cap on the tube where a snapping ring on the tube engages with a snap groove on the cap while maintaining a clearance between the cap and a top of the tube, wherein the snapping ring has at least one recess that provides an aerobic clearance between the tube and the cap when the cap is in the first position, thereby achieving an aerobic position where the tube is attached to the cap but unsealed;
   further turning the cap; and
   identifying a second area of friction which defines a second position where the tube is closed flush against the cap, thereby achieving an anaerobic position where the tube is fully sealed.

2. The method of claim 1, wherein the tube is a culture tube.

3. The method of claim 2, wherein the culture tube is a plastic culture tube.

4. The method of claim 1, wherein the cap is a plastic cap.

5. The method of claim 1, wherein the cap has a mating ring protruding from the cap underside that is configured to fit inside the tube rim to form the air-tight seal.

6. The method of claim 1, wherein identifying a second area of friction comprises turning the cap until the snap groove of the cap is past the snapping ring of the tube and a mating ring that protrudes from an underside of the cap is seated inside the open end of the tube to form a fluid-tight seal.

7. The method of claim 1, wherein identifying a second area of friction comprises turning the cap until the snap groove of the cap is past the snapping ring of the tube and an underside of the cap is seated against the rim of an open end of the tube to form a fluid-tight seal.

8. A method of closing a cap to a tube, comprising:
   placing a threaded cap on to a threaded end of a tube;
   turning the cap;
   identifying a first area of friction by seating a snapping ring of the tube in a snap groove of the cap, wherein the snapping ring and the snap groove are positioned to hold an underside of the cap a distance from a rim of the open end of the tube, and the snapping ring and threads of the tube are configured to define an air pathway between an inside of the tube and the exterior environment, thereby achieving an aerobic position where the tube is attached to the cap but unsealed;
   further turning the cap; and
   identifying a second area of friction, thereby achieving an anaerobic position where the tube is fully sealed.

9. The method of claim 8, wherein identifying a second area of friction comprises turning the cap until the snap groove of the cap is past the snapping ring of the tube and a mating ring that protrudes from an underside of the cap is seated inside the open end of the tube to form a fluidtight seal.

10. The method of claim 8, wherein identifying a second area of friction comprises turning the cap until the snap groove of the cap is past the snapping ring of the tube and an underside of the cap is seated against the rim of the open end of the tube to form a fluidtight seal.

11. The method of claim 8, wherein the tube is a culture tube.

* * * * *